United States Patent [19]

Hoshika et al.

[11] Patent Number: 4,540,253
[45] Date of Patent: Sep. 10, 1985

[54] METHOD AND DEVICE FOR MEASURING EYE REFRACTION ERRORS

[75] Inventors: Shuji Hoshika, Saitama; Hideyuki Ishiai, Tokyo; Yukiyasu Nishikawa, Saitama; Masato Hara, Tokyo; Hirochika Aiura; Ikuzo Okamoto, both of Saitama; Osamu Shindow, Tokyo, all of Japan

[73] Assignee: Asahi Kogaku Kogyo Kabushiki Kaisha, Tokyo, Japan

[21] Appl. No.: 635,472

[22] Filed: Jul. 30, 1984

Related U.S. Application Data

[63] Continuation of Ser. No. 262,663, May 11, 1981, abandoned.

[30] Foreign Application Priority Data

May 12, 1980 [JP] Japan ............................ 55-64756[U]
May 27, 1980 [JP] Japan ................................ 55-70338

[51] Int. Cl.$^3$ .............................................. A61B 3/14
[52] U.S. Cl. ................................................... 351/211
[58] Field of Search .......................... 351/211, 221, 214

[56] References Cited

U.S. PATENT DOCUMENTS 3,883,233  5/1975  Guilino et al. ...................... 351/211
3,888,569  6/1975  Munnerly et al. .................. 351/211
4,293,199 10/1981  Wada .................................. 351/211

Primary Examiner—Rodney B. Bovernick
Attorney, Agent, or Firm—Sughrue, Mion, Zinn, Macpeak, & Seas

[57] ABSTRACT

A method and apparatus for measuring eye refraction errors in which a plurality of infrared patterns are projected onto an eye to be measured. The reflected light is directed onto corresponding light sensitive detectors the outputs of which are coupled through bandpass filters, an automatic gain control circuit and an A/D converter to a microprocessor. The microprocessor analyses the digitized outputs calculating refraction powers in accordance with a disclosed nonlinear regression technique. The refraction errors of the eye, along with a reliability coefficient, are calculated in accordance with the thusly determined refraction powers.

12 Claims, 9 Drawing Figures

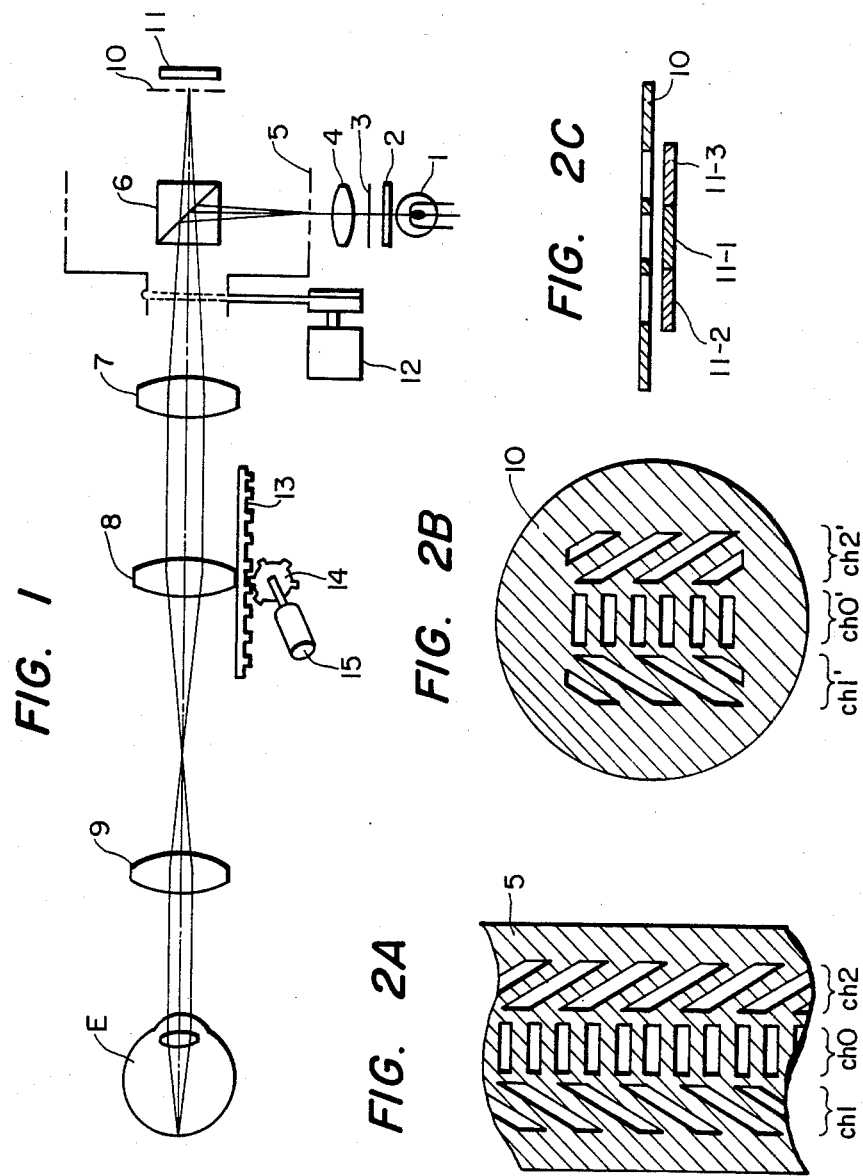

METHOD AND DEVICE FOR MEASURING EYE REFRACTION ERRORS

This application is a continuation of application Ser. No. 262,663, filed May 11, 1981 now abandoned.

BACKGROUND OF THE INVENTION

The present invention relates to a method and a device for measuring and calculating refraction errors of the eye.

The refraction error of an eye is represented by the refracting power of a lens which would compensate for the refraction irregularity. More specifically, the error is represented by a spherical power (S), a cylindrical power (C) and a cylinder axis ($\theta$) of the cylindrical surface. There is a mathematical relation between the refracting power (R) and the abovementioned values as follows: PS $$R = S + C \cdot \sin^2(\theta - \alpha),$$

wherein $\alpha$ represents a measured meridian angle. Thus, it is possible to obtain refraction errors (S, C, $\theta$) from at least three data points measured for the meridian angle and the refraction power R.

In a prior art eye refraction error measuring apparatus there is a difficulty in obtaining a signal having a sufficiently high S/N (signal/noise) ratio because the reflected light from the retina of the eye is extremely weak and it includes a considerable amount of noise components such as light reflected from the cornea and the like. There is also a problem in obtaining measured results of high reliability.

Japanese Published Patent Application No. 2519/79 discloses an apparatus which attempts to overcome such difficulties. In this apparatus, the meridian angle $\alpha$ to be measured can be varied within a wide range, measured results of a signal representing a refraction value corresponding to an optimum focal point at each meridian angle are simulated by a sine wave, and refraction errors are calculated from the sine wave. In order to assure accurate calculation results, the difference between the signal and the sine wave is analyzed prior to the calculation of the refraction errors. If the difference is found to be excessive, this fact is indicated to the operator, and when the difference is sufficiently small, the calculated refraction errors are printed.

However, when it is desired to obtain refraction values for several meridian angles, the measuring system of the apparatus must be rotated for each different angle thus requiring considerable time for obtaining the necessary data (30 sec. is required for collecting data and processing the data). During the measurement, the eye must be kept at rest and focussed at infinity. When the measuring time becomes long, such a condition is hardly attainable resulting in deviations in the measured data and making it difficult to obtain reliable results. Furthermore, with this apparatus, there is no assurance of obtaining reliable refraction values $R_i (i=1, 2, 3, \ldots)$ from the data measured at meridian angles $\alpha_i$ thus making it difficult to obtain reliable results.

The eye refraction error measuring method and device according to the invention are intended to overcome these difficulties.

SUMMARY OF THE INVENTION

Accordingly, the invention provides a method for measuring eye refraction errors and an apparatus for carrying out this method. The method includes the steps of directing a plurality of types of energy patterns onto an eye to be measured. The energy patterns may be infrared light divided through rotating slits. Image conditions of the reflected light from the retina of the eye are detected to produce data representing the image conditions. From this data, a nonlinear regression is performed to determine refraction powers. From the refraction powers, the refraction errors of the eye are determined.

The apparatus of the invention specifically may include a microprocessor, an automatic gain control circuit controlled by the microprocessor, an analog-to-digital converter receiving an output from the automatic gain control circuit and producing digital inputs to the microprocessor, an indicating device and a printing device for indicating errors and printing eye refraction errors. In accordance with the invention, a reliability coefficient is calculated. If the reliability coefficient is smaller than a predetermined value, an indication to the operator is produced.

BRIEF DESCRIPTION OF THE DRAWINGS

FIG. 1 is a diagram showing an example of an optical system to which the present invention is advantageously applied;

FIGS. 2A, 2B and 2C are diagrams showing patterns of a scanning chart and a fixed chart and an example of a light receiving element, respectively;

DESCRIPTION OF THE PREFERRED EMBODIMENTS

Figures 3, 4:
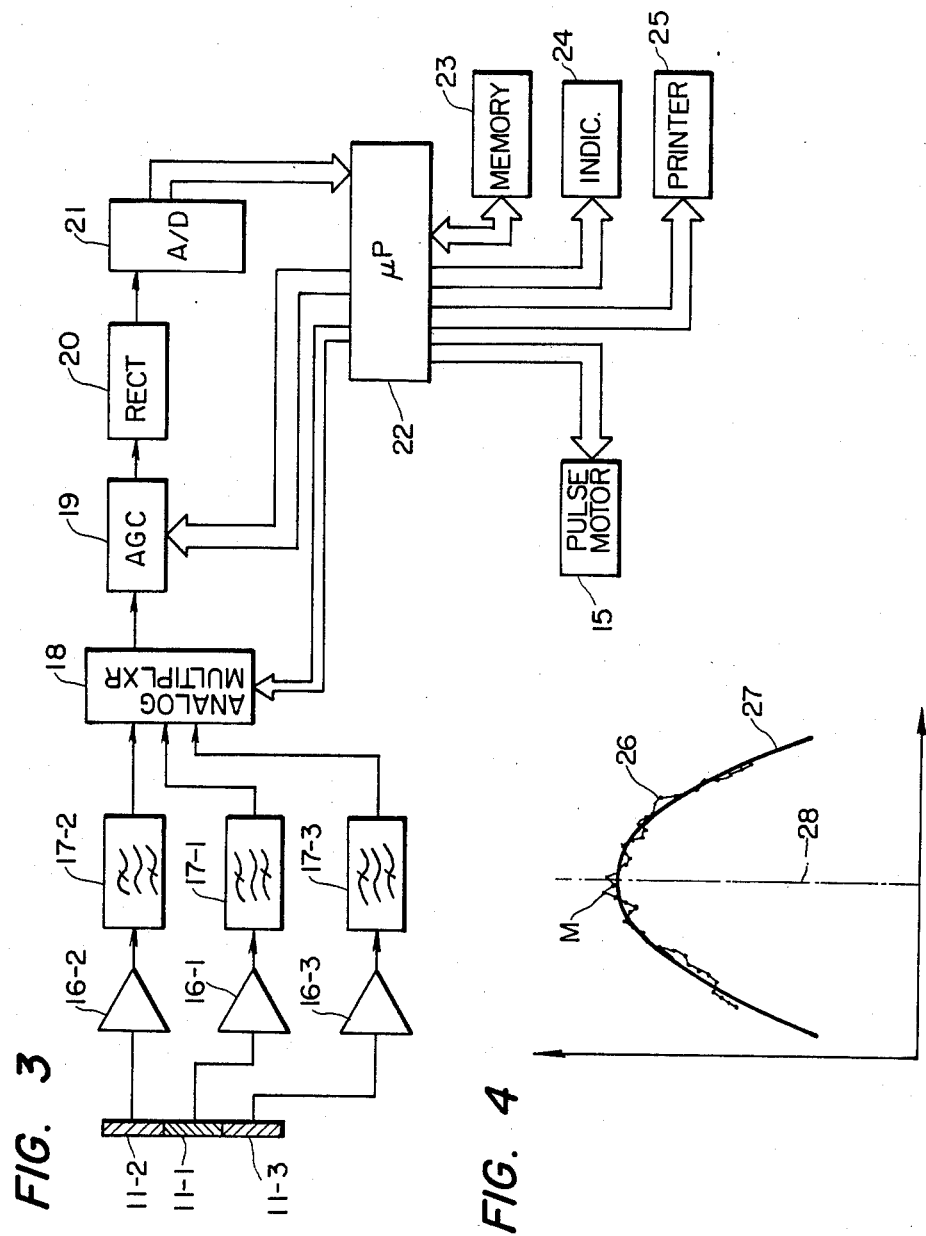
FIG. 3 is a block diagram of a preferred embodiment of the present invention.
FIG. 4 is a graphical representation showing an example wherein data in terms of a specific meridian angle are indicated together with a quadratic curve to which regression is effected from the data.

FIG. 1 shows an example of an optical system of an eye refraction error measuring device constructed in accordance with the present invention. Light rays emitted from a light source 1 are diffused by a diffusion plate 2. The light rays thus diffused pass through an infrared filter 3 so that only those rays having wavelengths longer than, for instance, 850 $\mu$m are allowed to pass a condenser lens 4. The rays then pass through a scanning chart 5 to a beam splitter 6. One part of the light rays reflected from the beam splitter 6 passes through a collimator lens 7, a movable lens 8 and an objective lens 9 to an eye E the refraction errors of which are to be measured. The light rays reflected from the retina of the eye E pass back through the above described lenses to the beam splitter 6. One part of the light rays entering the beam splitter 6 advances straight through a fixed chart 10 to a light receiving device 11. The scanning chart 5 and the fixed chart 10 are placed at positions conjugate with each other with respect to the beam splitter 6, which positions are backward focal points (the forward and backward directions are defined with reference to the eye E) of the collimator lens 7.

FIG. 2A shows an example of the pattern of the scanning chart 5 which has a cylindrical configuration and which is placed around the optical axis of the lens system so as to be rotated by a motor 12. The pattern of the chart 5 includes a part designated by ch0 which is perpendicular to the rotational direction of the scanning chart 5 and parts ch1 and ch2 forming angles ±60° with respect to the rotational direction of the chart 5. FIG. 2B shows an example of the pattern of the fixed chart 10. The pattern of the fixed chart 10 is quite similar to that of the scanning chart 5. In FIG. 2B, those parts corresponding to the parts ch0, ch1 and ch2 of the scanning chart 5 are designated by ch0', ch1' and ch2', respectively. The parts ch0 (ch0'), ch1 (ch1') and ch2 (ch2') are provided for carrying out the eye refraction error measurement at meridian angles of 90°, 150° and 30°, respectively. Herein it is assumed that the meridian angles are measured counterclockwisely from the horizontal direction.

Furthermore, the light receiving device 11 is composed of three light receiving elements 11-1, 11-2 and 11-3 to separately receive the light rays which have passed through the channels ch0', ch1' and ch2') of the fixed chart 10 as shown in FIG. 2C. The movable lens 8 is movable along the optical axis forwardly and backwardly. Such a construction can be realized by providing, for instance, a spur gear 13 on the frame supporting the lens and by driving a gear 14 meshing with the spur gear with a pulse motor 15.

With the above described construction of the optical system, if the images of the patterns (ch0, ch1 and ch2) of the scanning chart 5 are focused on the retina by adjusting the position of the movable lens 8, the positional relation between the retina and the scanning chart 5 and the fixed chart 10 is a conjugate relation, rendering the AC output produced due to the rotation of the scanning chart from the light receiving device 11 a maximum. When the movable lens 8 is moved to a position forward or backward of the above described position, the AC output of the light receiving element is reduced.

If the eye to be measured has no cylindrical component, the three light receiving elements 11-1, 11-2 and 11-3 deliver maximum AC outputs at the same position of the movable lens 8. However, when a cylindrical component exists in the eye E, the light receiving elements 11-1, 11-2 and 11-3 produce maximum AC outputs at different positions of the movable lens 8.

Since the refraction powers R of the eye can be defined with respect to the positions of the movable lens 8, the refraction errors (S, C and $\theta$) can be obtained by determining the positions of the movable lens 8 delivering maximum AC outputs from the light receiving elements 11-1, 11-2 and 11-3 for meridian angles of $\alpha = 90°$, 150° and 30°. That is, refraction powers $R_{90}$, $R_{150}$ and $R_{30}$ are calculated by solving the equations:

$$R_{90} = S + C \cdot \sin^2(\theta - 90°),$$

$$R_{150} = S + C \cdot \sin^2(\theta - 150°),$$

and $$R_{30} = S + C \cdot \sin^2(\theta - 30°).$$

In the described preferred embodiment, the refraction powers $R_{90}$, $R_{150}$ and $R_{30}$ at meridian angles $\alpha = 90°$, 150° and 30° can be obtained by simply reciprocating the movable lens once. Therefore, the measuring period is substantially reduced. For example, the required data can be obtained within a period of less than 5 sec.

A method and a device for obtaining reliable refraction values $R_{90}$, $R_{150}$ and $R_{30}$ from the data thus measured with respect to meridian angles ($\alpha = 90°$, 150° and 30°) will now be described. In an embodiment shown in FIG. 3, the AC outputs from the light receiving elements 11-1, 11-2 and 11-3 are amplified by preamplifiers 16-1, 16-2 and 16-3. Then frequency components corresponding to relative movement between the scanning chart 5 and the fixed chart 10 are extracted by bandpass filters 17-1, 17-2 and 17-3 from the thus amplified outputs. An analog multiplexer 18 selects and passes one of the outputs corresponding to ch0, ch1 and ch2 under the control of a microprocessor 22 with the selected component coupled to an AGC (automatic gain control) circuit 19. The output of the AGC circuit 19 is converted by a rectifying circuit 20 into a DC output which is then converted by an A/D (analog/digital) converter 21 into a digital value which is received by the microprocessor 22.

As examples, in the device of FIG. 3, the light receiving elements 11-1, 11-2 and 11-3 can be implemented with a Siemans Co. type BPW34 device, the preamplifiers 16-1, 16-2 and 16-3 with a National Semiconductor Co. type LF356, the bandpass filters with a National Semiconductor Co. type LF356, the analog multiplexer 18 with an Analog Devices Co. type AD7501, the AGC circuit 19 with an Analog Devices Co. type AD7524, the rectifying circuit 20 with an RCA Co. type MA741, the A/D converter 21 with an Analog Devices Co. type AD570, the microprocessor 22 with an Intel Co. type I8085 and the memory 23 with an Intel Co. type I2114.

The reason for providing the AGC circuit 19 will now be described. If the A/D converter 21 were to be required to accept the full range of output of the light receiving element 11, a high resolution would be essential. However, since a resolution of, for instance, 8 bits at the maximum output of the reflected light from the retina of the eye E is sufficient for the present device, correct operation of the A/D converter 21 can be obtained by reducing the gain value set by the AGC circuit 19 when the output of the light receiving element 11 exceeds the full scale (equivalent to a digital output of $2^8$) of the A/D converter 21.

The procedure for obtaining data required for determining refraction values $R_{90}$, $R_{150}$ and $R_{30}$ will next be described. Required data are the positions of the movable lens 8 and the outputs of the light receiving elements 11 for each position of the movable lens 8. Firstly, the pulse motor 15 is rotated under the direction of the microprocessor 22 so as to move the movable lens 8 to a forwardmost (toward the measured eye) position. Then the pulse motor 15 is rotated in reverse so as to move the movable lens 8 backwardly (away from the measured eye). During the backward movement of the movable lens 8, maximum values of the outputs of the light receiving elements 11-1, 11-2 and 11-3 are measured and the gain of the AGC circuit 19 is set to an appropriate value. Assuming an effective range where the output of a light receiving element is more than one-half of the maximum value, the movable lens 8 is moved rearwardly until either one of the outputs of the light receiving elements is out of the effective range.

Then the pulse motor 15 is rotated in a direction shifting the movable lens 8 forwardly (toward the eye) until all of the outputs of the light receiving elements are out of their effective ranges. During the movement of the movable lens 8, the positions of the movable lens 8 where the output of a light receiving element is within its effective range and the values of the output at those positions are stored for each of the light receiving elements in a memory device 23 through the microprocessor 22. Thus, by one reciprocating movement of the movable lens 8 the collection of all the data required for determining the refraction values $R_{90}$, $R_{150}$ and $R_{30}$ can be accomplished for all three channels so that the patient is spared from the discomfort accompanying the prior art procedure.

A procedure for improving the reliability of the refraction values $R_{90}$, $R_{150}$ and $R_{30}$ thus obtained by nonlinear regression on the measured data will now be described. Near the maximum output position, a nonlinear regression curve is assumed for the relation between the intensity of light reflected from the retina and the position of the movable lens 8. It is further assumed that $d_i$ represent values of the output data thus collected in the effective range, $r_i$ represent values of refraction corresponding to the values of the output data (i = 1, 2, . . . , n), and that the equation defining the regression curve is:

$$D = \alpha_0 + \alpha_1 R + \alpha_2 R^2,$$

where D is the output data. The coefficients $\alpha_0$, $\alpha_1$ and $\alpha_2$ can be obtained from the solution of the following simultaneous equations:

$$\alpha_0 n + \alpha_1 \sum_i r_i + \alpha_2 \sum_i r_i^2 = \sum_i d_i$$

$$\alpha_0 \sum_i r_i + \alpha_1 \sum_i r_i^2 + \alpha_2 \sum_i r_i^3 = \sum_i d_i r_i$$

$$\alpha_0 \sum_i r_i^2 + \alpha_1 \sum_i r_i^3 + \alpha_2 \sum_i r_i^4 = \sum_i d_i r_i^2$$

By carrying out these computations, regression of the data collected in the effective range to an optimum quadratic equation is performed. The solution of the simultaneous equations is easily carried out by the microprocessor 22 which is provided with programs to be used for the solution.

FIG. 4 is a graph showing an example of data thus collected from a specific channel falling in the effective range together with the quadratic regression curve. The ordinate represents the output data D and the abscissa represents the position of the movable lens 8 (corresponding to the refraction value). In FIG. 4, the line 26 connecting data point dots represents actual values of the output data in the effective range, and solid line 27 shows the optimum quadratic regression curve obtained from this data.

In a case where the regression curve is not used and the position of the movable lens 8 delivering a peak value of the output data is determined to be refraction value R, the peak position M in FIG. 4 is taken as the refraction value R. Using the regression curve 27 the refraction value R is defined by a dot chain line 28. As the above-described decision is executed in accordance with the method of least squares from various data values, the resultant value of the refraction R is far more reliable than a value obtained from the peak position M.

More specifically, the maximum position of the regression curve is selected to be the position of the movable lens 8 delivering the maximum output of the light reflected from the retina of the eye E for one specific channel, and the refraction values $R_{90}$, $R_{150}$ and $R_{30}$ can be obtained by executing the regression for three channels.

As described hereinbefore, since the refraction values $R_{90}$, $R_{150}$ and $R_{30}$ are obtained utilizing regression curves in accordance with the method of least squares from a number of data points, the reliability of the refraction values is much higher than can be obtained from the maximum values of the data directly without regression.

Furthermore, a normal distribution function expressed by $D = \alpha_0 \cdot \exp\{-\alpha_1(R - \alpha_2)^2\}$ may also be used for the regression curve.

Since the refraction errors of eye (S, C and $\theta$) are obtained from the refraction values $R_{90}$, $R_{150}$ and $R_{30}$ as described above, these refraction values are highly reliable so that the refraction errors can be accurately determined.

The reliability of the refraction values obtained using the regression curve can be indicated by the difference between the regression curve and the data thus collected. Assuming the equation representing the regression curve for a channel to be $D = \alpha_0 + \alpha_1 R + \alpha_2 R^2$, the difference S is expressed as:

$$S = \sqrt{\frac{\sum_i \{d_i - (\alpha_0 + \alpha_1 R + \alpha_2 R^2)\}^2}{n - 1}}$$

The difference is calculated by the microprocessor 22 for each channel, and a reliability coefficient L for the refraction errors to be determined by the device of the present invention is defined by the sum of the differences calculated for the three channels. If the differences for the three channels ch0, ch1 and ch2 are represented by $S_0$, $S_1$ and $S_2$, respectively, the reliability coefficient L is expressed as:

$$L = S_0 + S_1 + S_2.$$

Thus it is apparent that the reliability for the measured results of the refraction errors is high when the reliability coefficient L is low.

Figure 5:
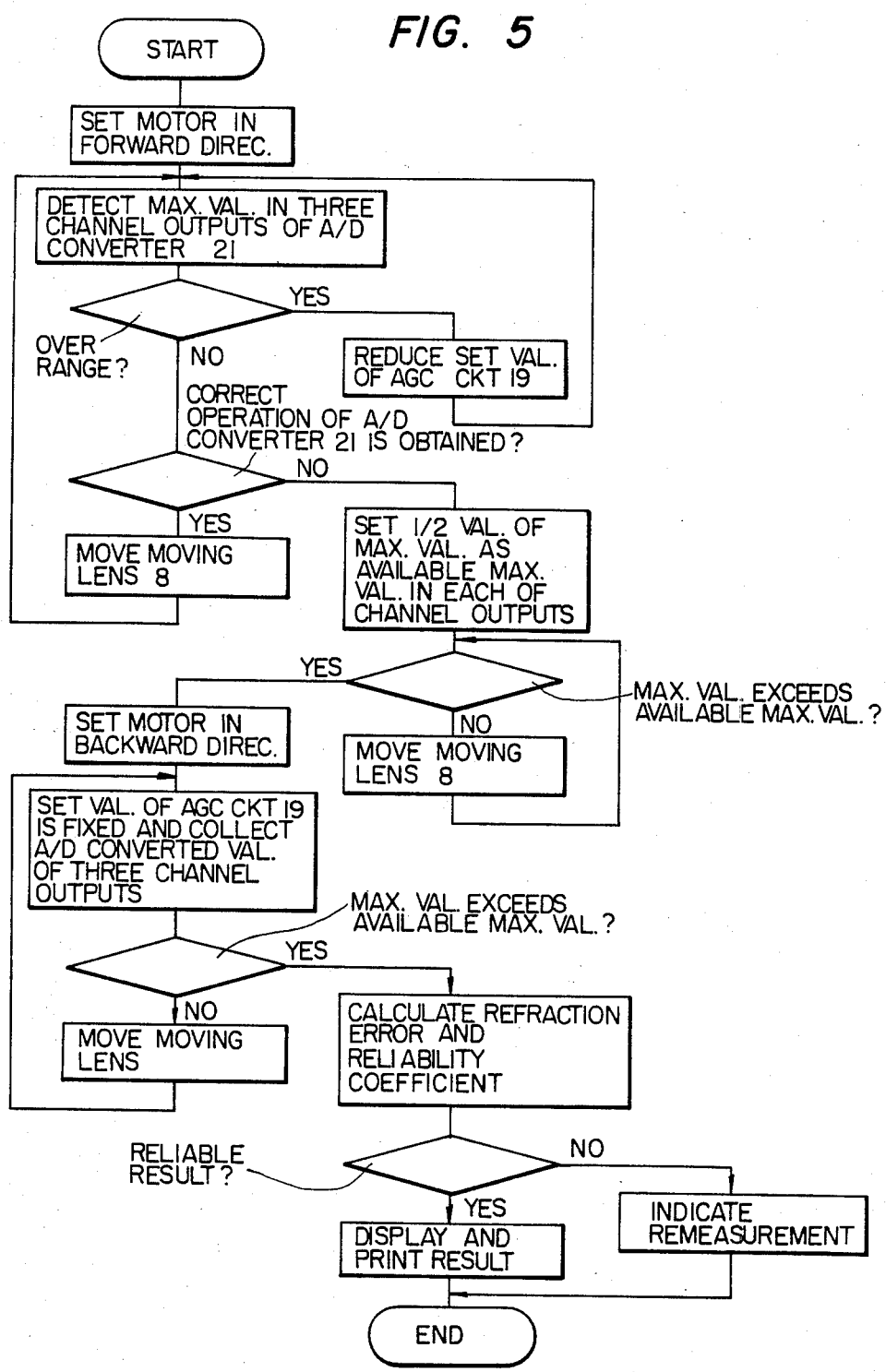
FIG. 5 is a flow chart detailing operations performed by a microprocessor in the circuit of FIG. 3.

The above-described calculation can be easily carried out by the microprocessor. FIG. 5 is a flow chart of the overall operation of the microprocessor and the peripheral units.

The reliability coefficient and the refraction errors of the eye are indicated to the operator of the device as follows.

If the reliability coefficient is smaller than a specific value, the measured refraction errors are indicated on an indicating device 24 as S, C and $\theta$ which are simultaneously printed by a printer 25. However, if the reliability coefficient L is larger than the predetermined specific value, the measured refraction errors are not reliable. In this case, the need for repeating the measurement operation is indicated by, for example, repeatedly flashing the measured results of the refraction errors on the indicating device 24 or in another manner as desired.

According to the method and device of the invention, since the data with respect to three meridian angles can be collected during one reciprocation of the movable lens, the advantageous feature of shortening the measuring time so that the eye being measured need not be held stationary for a long period of time is provided.

Furthermore, the invention provides another advantageous feature of regressing the measured data to a nonlinear curve thereby providing refraction values of a high reliability from data collected from very weak signal light. Still another advantageous feature is the provision of a reliability coefficient L from the difference between the regression curve and the measured data. By observing the reliability coefficient on an indicator, the operator of the device is assured of the reliability of the measurement.

Modifications can be made to the embodiments described within the scope of the invention. For instance, in the modified optical system shown in FIG. 6, smaller light receiving elements 11-1, 11-2 and 11-3 may be used leading to a reduction in output noise.

In this optical system, two trigonal prisms 30-1 and 30-2 having an appropriate apex angle are arranged immediately after the fixed chart 10 at positions so as to cover the pattern regions at both ends of the fixed chart 10 with the apexes of the prisms opposite one another. Furthermore, a light converging lens 31 having a short focal length is provided after the two trigonal prisms 30-1 and 30-2, and three light receiving elements 11-1, 11-2 and 11-3 are arranged at positions conjugate with respect to the light converging lens 31 with the collimator lens 7 with an appropriate spacing being provided therebetween.

The two trigonal prisms 30-1 and 30-2 and the light converging lens 31 focus an image of a reduced size from the collimator lens 7 on each of the light receiving elements 11-1, 11-2 and 11-3. Without the trigonal prisms 30-1 and 30-2, light passing through the three types of patterns of the fixed chart 11 would tend to be converged on the center one of the light receiving elements making it difficult to separate light passing through the patterns and to process the light components in parallel. In other words, the trigonal prisms 30-1 and 30-2 are inserted for separating the light components passing through the three types of patterns of the fixed chart 10 from each other and for processing the components in parallel.

Figure 6:
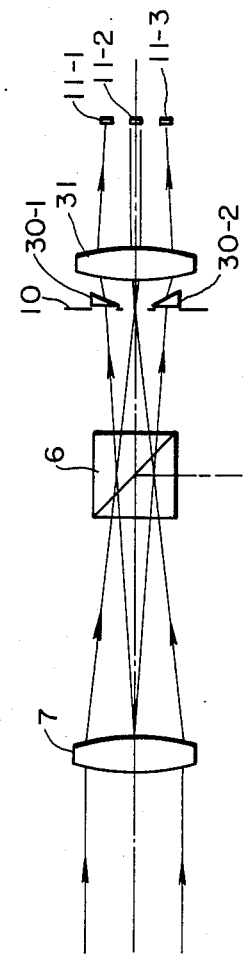
FIGS. 6 and 7 are diagrams showing modifications of the optical system shown in FIG. 1.
Figure 7:
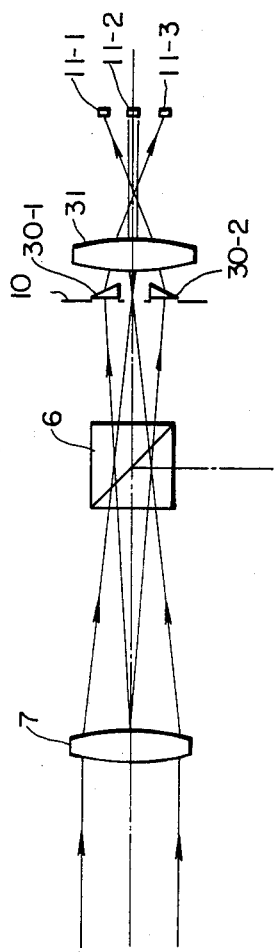

FIG. 7 shows yet another embodiment in which the trigonal prisms 30-1 and 30-2 are set with the apexes of the two prisms facing outwardly. The effects of this embodiment are substantially the same as for the embodiment described with reference to FIG. 6.

In the embodiments shown in FIGS. 6 and 7, although charts having three types of patterns have been considered, it is apparent to those skilled in the art that the types of the patterns are not necessarily restricted to three.

With the above described construction of the optical system in the light receiving part of the apparatus, the light receiving areas of the light receiving elements are defined by the image reducing ratio of the light converging lens thus making it possible to use light receiving elements having light receiving areas of a substantially reduced size. As a result of the reduction in size of the light receiving areas, noise generated by the light receiving elements themselves is substantially reduced. Furthermore, since light receiving elements of small sizes and normal constructions can be used effectively, the manufacturing cost of the light receiving elements can be reduced. As an additional advantageous effect, the time required for measurement is further shortened and the reliability of the eye refraction measuring apparatus further substantially improved.

What is claimed is:

1. An eye refraction error measuring apparatus comprising a light source; means for directing light from said light source and a plurality of patterns onto an eye to be measured; at least one light receiving element receiving light refracted from the retina of said eye; an automatic gain control circuit for determining a gain factor of an output signal from said light receiving element; analog-to-digital converter means for converting an output of said automatic gain control circuit to digital data; a microprocessor receiving digital data from said analog-to-digital converter means for performing nonlinear regression upon outputted data from said analog-to-digital converter, for determining eye refraction errors in accordance with results of said nonlinear regression, for determining a reliability coefficient, and for determining when said reliability coefficient is less than a predetermined value; and visual displaying means, said microprocessor operating said displaying means to display said eye refraction errors when said reliability coefficient is greater than said predetermined value and for producing an indication to an operator when said reliability coefficient is less than said predetermined value.

2. The eye refraction error measuring apparatus of claim 1 wherein said nonlinear regression is performed in accordance with a quadratic function.

3. The eye refraction error measuring apparatus of claim 1 wherein said nonlinear regression is performed in accordance with a normal distribution function.

4. An eye refraction error measuring apparatus comprising a light source; a diffusion plate, an infrared filter, and a condenser lens disposed in that order from said light source; a rotatable scanning chart having first through third parts of different patterns formed therein, light from said condenser lens being shone onto said scanning chart; a beam splitter positioned within said rotatable scanning chart; a collimator lens disposed to receive a first portion of light from said beam splitter; a movable lens disposed to receive light from said collimator lens; an objective lens for focusing light from said movable lens onto an eye to be measured; a fixed chart having a pattern similar to said rotatable scanning chart disposed to receive light reflected from the retina of said eye through said objective lens said movable lens, said collimator lens and said beam splitter; first through third light receiving elements disposed adjacent said fixed chart on a side thereof opposite said beam splitter; first through third preamplifiers each having an input, respectively, coupled to outputs of said first through third light receiving elements; first through third bandpass, filters having inputs, respectively, coupled to outputs of said first through third preamplifiers; an analog multiplexer having first through third inputs coupled to outputs of said first through third bandpass filters; an automatic gain control circuit having an input coupled to an output of said analog multiplexer; rectifier means having an input coupled to an output of said automatic gain control circuit; an analog-to-digital converter having an analog input coupled to an output of said rectifier means; a microprocessor having data inputs coupled to outputs of said analog-to-digital converter, said microprocessor being coupled to control said automatic gain control circuit and said analog multiplexer wherein said outputs from said first through third bandpass filters are coupled in sequence to said input of said automatic gain control circuit and wherein a gain factor of said automatic gain control circuit is set in accordance with a received signal value to output an analog signal having an amplitude within a predetermined range; a memory coupled to said microprocessor; indicator means coupled to said microprocessor; and printer coupled to said microprocessor, wherein said microprocessor is programmed to perform nonlinear regression upon input data received from said analog-to-digital converter to determine reliable refraction power values, to determine refraction errors of said eye from said refraction power values, to determine a reliability coefficient, to determine whether said reliability coefficient is larger than a predetermined value, means to print said refraction errors when said reliability coefficient is larger than said predetermined values and to operate said indicating means when said reliability coefficient is less than said predetermined value.

5. The eye refraction error measuring apparatus of claim 4 wherein said microprocessor performs said nonlinear regression in accordance with a quadratic curve.

6. The eye refraction error measuring apparatus of claim 4 wherein said microprocessor performs said nonlinear regression in accordance with a normal distribution function.

7. The eye refraction error measuring apparatus of claim 4 further comprising first and second trigonal prisms disposed adjacent said fixed chart on a side thereof opposite said beam splitter and between said fixed chart and said light receiving elements; and a light converging lens disposed between said trigonal prisms and said light receiving element.

8. The eye refraction error measuring apparatus of claim 7 wherein apexes of said trigonal prisms are disposed opposite each other.

9. The eye refraction error measuring apparatus of claim 7 wherein apexes of said trigonal prisms are disposed outwardly.

10. An eye refraction error measuring apparatus comprising a light source; a diffusion plate, an infrared filter, and a condenser lens disposed in that order from said light source; a rotatable scanning chart having first through third parts of different patterns formed therein, light from said condenser lens being shone onto said scanning chart; a beam splitter positioned within said rotatable scanning chart; a collimator lens disposed to receive a first portion of light from said beam splitter; a movable lens disposed to receive light from said collimator lens; an objective lens for focusing light from said movable lens onto an eye to be measured; a fixed chart having a pattern similar to said rotatable scanning chart disposed to receive light reflected from the retina of said eye through said objective lens said movable lens, said collimator lens and said beam splitter; first through third light receiving elements disposed adjacent said fixed chart on a side thereof opposite said beam splitter; first and second trigonal prisms disposed adjacent said fixed chart on a side thereof opposite said beam splitter and between said fixed chart and said light receiving elements; and a light converging lens disposed between said trigonal prisms and said light receiving element.

11. The eye refraction error measuring apparatus of claim 7 wherein apexes of said trigonal prisms are disposed opposite each other.

12. The eye refraction error measuring apparatus of claim 7 wherein apexes of said trigonal prisms are disposed outwardly.

* * * * *